US012171670B2

(12) United States Patent
Puttlitz et al.

(10) Patent No.: US 12,171,670 B2
(45) Date of Patent: Dec. 24, 2024

(54) IMPLANT FOR REPAIRING SPINAL ANNULAR DEFECT, METHOD OF FABRICATING THE IMPLANT, AND METHOD OF REPAIRING THE DEFECT USING THE IMPLANT

(71) Applicant: COLORADO STATE UNIVERSITY RESEARCH FOUNDATION, Fort Collins, CO (US)

(72) Inventors: Christian M. Puttlitz, Fort Collins, CO (US); Mitchell Page, Richmond (NZ)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 116 days.

(21) Appl. No.: 18/030,462

(22) PCT Filed: Oct. 5, 2021

(86) PCT No.: PCT/US2021/053585
§ 371 (c)(1),
(2) Date: Apr. 5, 2023

(87) PCT Pub. No.: WO2022/076422
PCT Pub. Date: Apr. 14, 2022

(65) Prior Publication Data

US 2023/0372114 A1 Nov. 23, 2023

Related U.S. Application Data

(60) Provisional application No. 63/232,095, filed on Aug. 11, 2021, provisional application No. 63/087,534, filed on Oct. 5, 2020.

(51) Int. Cl.
*A61F 2/44* (2006.01)
*A61F 2/30* (2006.01)

(52) U.S. Cl.
CPC ............ *A61F 2/442* (2013.01); *A61F 2/3094* (2013.01); *A61F 2002/4435* (2013.01); *A61F 2002/4495* (2013.01)

(58) Field of Classification Search
CPC .................... A61F 2/3094; A61F 2/442; A61F 2002/4435; A61F 2002/4495
See application file for complete search history.

(56) References Cited

U.S. PATENT DOCUMENTS

2007/0150063 A1 6/2007 Ruberte et al.
2014/0180420 A1 6/2014 Gatt et al.
(Continued)

OTHER PUBLICATIONS

International Preliminary Report on Patentability issued in Intl. Appln. No. PCT/US2021/053585 mailed Apr. 20, 2023.
(Continued)

*Primary Examiner* — Nicholas J Plionis
(74) *Attorney, Agent, or Firm* — ROSSI, KIMMS & McDOWELL LLP

(57) ABSTRACT

A biocompatible implant, as well as method of fabricating the implant and repairing an annular defect in annulus fibrosus (AF) of an intervertebral disc (IVD) disposed in a functional spinal unit (FSU), includes an insert that provides faces that can interface with the defect to repair or treat the AF. The implant can deliver biological and mechanical factors to enhance healing in an annular defect and prevent recurrence of herniation symptoms. The implant can be fabricated using a hybrid of first fibrous scaffold structure including at least a first layer and a second layer of first fibers fabricated via three-dimensional fiber deposition (3FD) and second fibrous scaffold structure including a third layer and a fourth layer of second fibers formed via melt electrowriting (MEW). Suitable attachment methods, including bio-adhesives can be used to bond the implant to the IVD and/or FSU.

19 Claims, 6 Drawing Sheets

(56) References Cited

U.S. PATENT DOCUMENTS

| | | | | |
|---|---|---|---|---|
| 2014/0222152 | A1* | 8/2014 | Kaplan | A61L 27/3604 623/17.16 |
| 2018/0228938 | A1* | 8/2018 | McGuire | A61L 27/3662 |
| 2018/0360610 | A1* | 12/2018 | Patel | A61F 2/3872 |

OTHER PUBLICATIONS

International Search Report issued in Intl. Appln. No. PCT/US2021/053585 mailed Dec. 28, 2021.

Written Opinion issued in Intl. Appln. No. PCT/US2021/053585 mailed Dec. 28, 2021.

* cited by examiner

HYBRID 3DF/MEW SCAFFOLD

HYBRID 3DF/MEW SCAFFOLD

IMPLANT FOR REPAIRING SPINAL ANNULAR DEFECT, METHOD OF FABRICATING THE IMPLANT, AND METHOD OF REPAIRING THE DEFECT USING THE IMPLANT

This application is the National Phase entry of International Appln. No. PCT/US2021/053585, filed 5 Oct. 2021, which claims priority to U.S. Provisional applications 63/087,534 filed 5 Oct. 2020 and 63/232,095 filed 11 Aug. 2021, the disclosures of which are incorporated herein by reference.

BACKGROUND

Chronic low back pain due to intervertebral disc (IVD) herniation is one of the most prominent and burdensome disabilities in society. Frequently, the debilitating consequences of IVD herniation require surgical intervention, such as laminectomy with partial discectomy, lumbar interbody fusion, or IVD arthroplasty. But these methods of treating spinal herniation are palliative and are associated with high rates of symptomatic reherniation and/or revision surgeries, namely failing to both mitigate sciatic pain and re-establish long-term function of the spine. Accordingly, there is a widely acknowledged need for advanced surgical strategies to arrest the disease progression, restore physiologic function, and alleviate the severe pain associated with common IVD pathologies.

A variety of novel, tissue engineering (TE) biomaterials have been proposed for annulus fibrosus (AF) regeneration. These methods prevalently employ additive manufacturing methods to generate specific scaffolds, which are similar to scaffolding in construction sites. A scaffold can be defined as a mechanically competent structure designed to support the loading environment in which it is intended to be implemented. In this case, the scaffold is designed to replace a piece of annulus fibrosis (AF) tissue. That is, the scaffold is intended to have similar mechanical properties, namely stiffness and strength, as the IVD tissue. Examples thereof include sponges made from collagen or matrices made with polymers. The mechanical efficacy of these TE scaffolds is critical to afford essential structural support, functional performance, resilience to implant failure, and a micromechanical environment conducive for the generation and maintenance of the intended mature tissue. Biomimetic fibrous composite scaffolds with structural fibers that replicate the native collagen architecture are well suited to AF repair and have demonstrated some in vitro success. Additionally, biocompatible and biodegradable materials, such as polycaprolactone (PCL), are integral in TE to provide an initial support structure while also providing a temporal degradation profile to enhance tissue development and growth.

Total disc replacements with regenerative constructs have been evaluated in small animal models and large animal models. Animal models are invaluable evaluation platforms to translate novel orthopaedic treatments to human clinical applications. In particular, the ovine model for lumbar spine treatments is a widely accepted, well-established translational model that closely reflects the physiological scale and mechanical loading of the human spine. But effective implementation of engineered biomaterials to an IVD repair strategy remains elusive. When treating spinal herniation, degenerative changes can exist throughout the whole disc, yet the symptomatic region of the IVD is frequently limited to a smaller annular defect. An approach focused on localized regeneration of the AF defect may afford a less invasive solution to prevent reherniation than whole disc replacement. This approach, however, requires careful consideration of implant design and surgical attachment to maintain functional spinal biomechanics and implant loading that is conducive to tissue regeneration.

There remains an unresolved need to for an implant for IVD repair that can both elicit tissue regeneration and retain healthy spinal biomechanics to restore physiological function, as well as to alleviate pain associated with intervertebral disc herniation. The present invention addresses this need.

SUMMARY

One aspect of the present invention is a biocompatible implant. The implant can be used for repairing a defect in the AF of an IVD disposed in a functional spinal unit (FSU), which is a vertebra-IVD-vertebra construct. The implant includes an insert providing at least a first face and a second face, which is spaced from the first face, configured to interface with tissues in a gap occurring at the defect of the AF. The insert comprises a plurality of layers of fibrous material providing a first fibrous scaffold structure and a second fibrous scaffold structure that is different from the first fibrous scaffold structure.

The first fibrous scaffold structure includes a first layer of first fibers arranged spaced apart at a first spacing, and a second layer of additional first fibers arranged spaced apart at the first spacing and arranged an angle to the first fibers of the first layer. The first fibers can be made of a polymer, including PCL.

The second fibrous scaffold structure includes a third layer of second fibers arranged spaced apart at a second spacing, and a fourth layer of additional second fibers arranged spaced apart at the second spacing and arranged an angle to the second fibers of the third layer. The second fibers also can be a polymer, including PCL.

The second fibrous scaffold structure can be disposed over at least one of the first or second layer, between adjacent first fibers of the second or first layer, so that the second fibrous scaffold structure extends along a length of the adjacent first fibers of the second or first layer. The second fibrous scaffold structure can form a sheet, and the implant includes a plurality of sheets of the second fibrous scaffold structure fused to the first fibrous scaffold structure.

The first fibers can have a larger nominal diameter than the second fibers, and the first spacing can be larger than the second spacing. For example, the first spacing can be 1.0 mm and a nominal diameter of the first fibers can be a range of 100-500 μm, and the second spacing can be 0.1 mm and a nominal diameter of the second fibers can be in a range of 5-100 μm.

The insert can include a third face, a fourth face spaced from the third face, a fifth face, and a sixth face spaced from the fifth face. The third and fourth faces disposed between the first and second faces. The fifth face and the sixth face extend between the first, second, third, and fourth faces and form a hexahedron shape with six sides.

The first face and the second face can be spaced apart in a circumferential direction of the IVD, in a state where the insert is disposed in the AF. Alternatively, the first face and the second face can be spaced apart in an axial direction of the IVD, in the state where the insert is disposed in the AF.

The implant can further include a plate connected to the insert, and disposed on a side of the sixth face. The plate also can include the first fibrous scaffold structure and the second fibrous scaffold structure. The plate can include upper and lower wings configured to secure to the FSU that includes the IVD to be repaired. The upper and lower wings can extend axially outwardly respectively from a side of the third face and a side of the fourth face.

Another aspect of the present invention is a method of fabricating the implant. The method includes forming the first fibrous scaffold structure including the first layer and the second layer by forming the first layer by arranging the first fibers spaced apart at the first spacing and forming the second layer over the first layer by arranging the additional fibers spaced apart at the first spacing at an angle to the first fibers of the first layer.

The fabricating method further includes forming each of a plurality of sheets of the second fibrous scaffold structure including the third layer and the fourth layer by forming the third layer by arranging the second fibers that have a smaller nominal diameter than the first fibers spaced apart at the second spacing that is smaller than the first spacing, and forming the fourth layer over the third layer by arranging the additional second fibers spaced apart at the second spacing at an angle to the second fibers of the third layer.

The fabricating method further includes disposing one sheet, among the plurality of sheets of the second fibrous scaffold structure, over at least the first or second layer, between adjacent first fibers of the second or first layer, so that the one sheet extends along a length of the adjacent first fibers of the second or first layer. The first and second layers can be formed by three-dimensional fiber deposition, and the third and fourth layers can be formed by melt electrowriting.

The fabricating method can further includes heating the implant to fuse the sheets of the second fibrous scaffold structure to the first fibrous scaffold structure.

Another aspect of the present invention is a method of repairing an annular defect in the AF of the IVD using the implant. The repairing method includes disposing the insert inside the gap at the defect of the AF so that the first face and the second face interface with adjacent tissues at the gap and the first face and the second face are spaced along a circumferential direction of the IVD, and securing the insert to the FSU.

The repairing method further includes securing, using bio-adhesive, at least one of (a) the first face and the second face to the IVD or (b) the third face and the fourth face to the IVD. Each of the third face and the fourth face can be configured to interface with one of cartilaginous endplates of the IVD at top and bottom sides thereof.

The method further includes securing the upper and lower wings to the FSU using at least one of fixation hardware (such as bone screws) or bio-adhesive.

The method further includes securing, using bio-adhesive, any of the first face and the second face to the IVD, the third face and the fourth face to the IVD, and the upper and lower wings to the FSU.

BRIEF DESCRIPTION OF THE DRAWING

In FIGS. 8A-8D, the x- and y-directions respectively represent the axial and circumferential directions in relation to the IVD.

DETAILED DESCRIPTION

A biocompatible implant 10, 10A (hereafter "implant" for brevity) can be tissue engineered to repair or treat an AF, for example, to repair a herniated section of a defect IVD. The implant can deliver biological and mechanical factors to enhance healing in the annular defect (hereafter "defect" for brevity) and prevent recurrence of herniation symptoms. Specifically, the implant is tissue engineered to allow tissues to regenerate around and within the implant. In particular, the present implant 10, 10A can be fabricated using a 3D printed lattice that is designed to mimic the mechanical properties of the IVD's AF.

The implant is configured or shaped to be inserted into the cavity of the IVD defect and can provide regenerative potential. Although the implant can be used to treat the posterior and posterolateral aspects of a large animal, including human lumbar IVDs, the implant also can be applied to any annular positions, any intervertebral disc level, and any vertebrate species.

Figure 1:
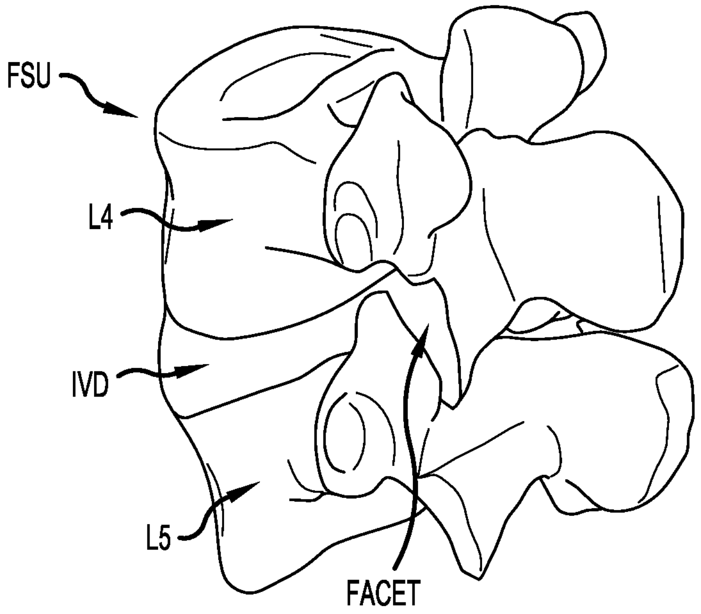
FIG. 1 graphically illustrates a functional spinal unit (FSU) at a lumbar region, which FSU includes an intervertebral disc (IVD) sandwiched between upper and lower vertebral bodies of, for example, L4-L5 vertebrae.

FIG. 1 graphically illustrates a functional spinal unit (FSU) at a lumbar region, which includes an IVD sandwiched between upper and lower vertebral bodies, namely L4-L5 vertebrae for example. The implant 10, 10A is configured to be anchored to the FSU so that mechanical loads from the body can be transferred to the implant. The loading to the implant (1) provides mechanical support for the spine, (2) maintains sufficient mechanical compliance for healthy biomechanical functional of the spine, and (3) generates a micromechanical environment within the scaffold configuration of the fibers that stimulates tissue regeneration. The implant thus can elicit tissue regeneration in the defect to prevent symptomatic recurrence of disc herniation and maintain full spinal motion.

Figure 2A:
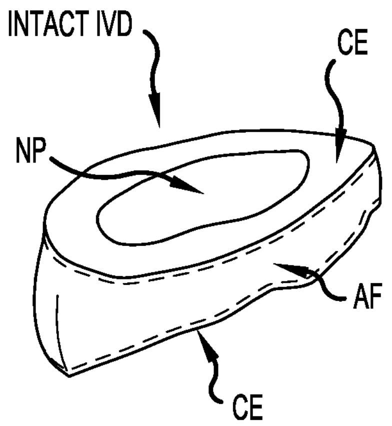
FIG. 2A graphically illustrates an intervertebral disc (IVD) of FIG. 1 with no defect (intact IVD) between the L4-L5 vertebrae.
Figure 2B:
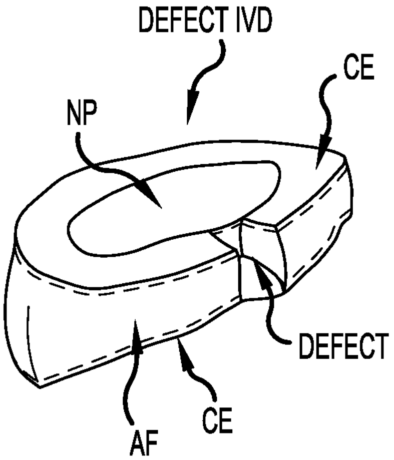
FIG. 2B graphically illustrates the IVD of FIG. 2A with an annular defect (defect IVD).
Figure 3A:
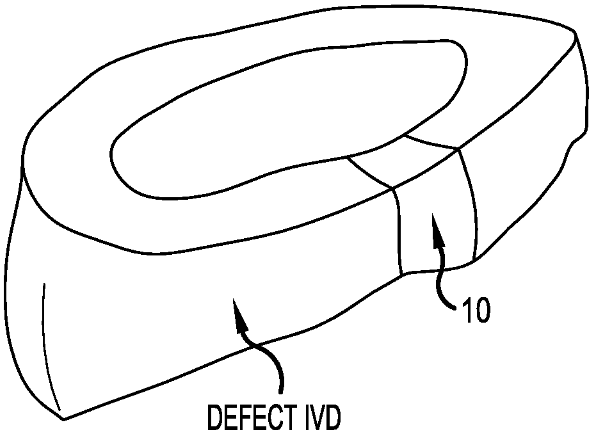
FIG. 3A graphically illustrates the defect IVD of FIG. 2B with a plug implant inserted into the area of the defect.
Figure 3B:
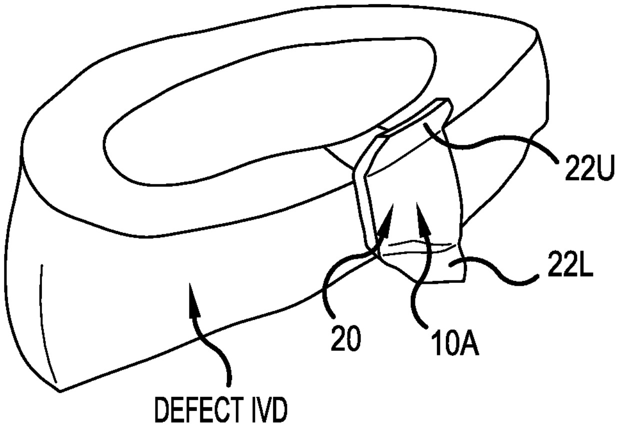
FIG. 3B is similar to FIG. 3A, except that a plate implant is inserted rather than the plug implant.

FIG. 2A graphically illustrates an intact (healthy) IVD, which is composed of nucleus pulposus (NP) at the core, annulus fibrosus (AF) surrounding the NP, and cartilaginous endplate (CE) (shown in phantom) at each of the top and bottom sides. FIG. 2B graphically illustrates the defect IVD with the defect, which is an annular fissure or tear through one or more layers of the AF (posterolateral aspect). In FIG. 2B, the defect is graphically illustrated as a geometric (e.g., cutout) cavity rather than as an actual fissure or tear. FIG. 3A graphically illustrates the defect IVD of FIG. 2B with a plug implant 10 inserted into the cavity of the defect. FIG. 3B is similar to FIG. 3A, except that a plate implant 10A is inserted rather than the plug implant 10.

Figure 4A:
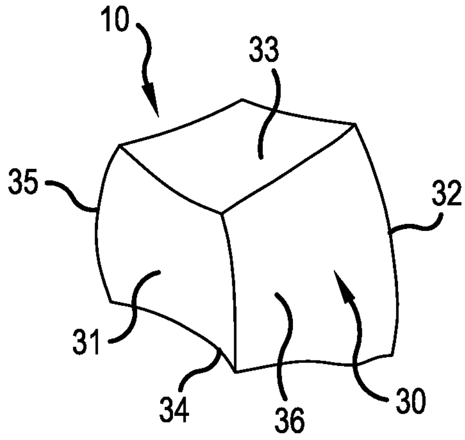
FIG. 4A graphically illustrates a perspective view the plug implant from the outer (proximal) side.
Figure 4B:
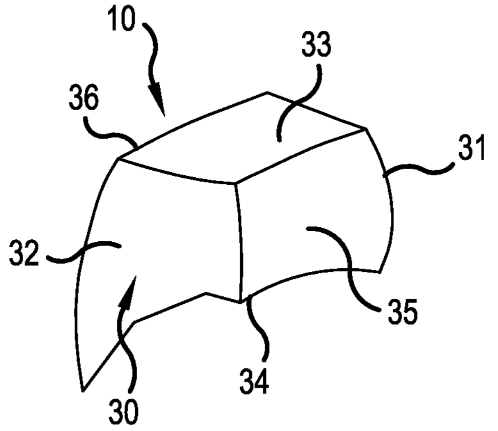
FIG. 4B graphically illustrates another perspective view of the plug implant of FIG. 4A from the opposite (distal) side of the plug implant.
Figure 5A:
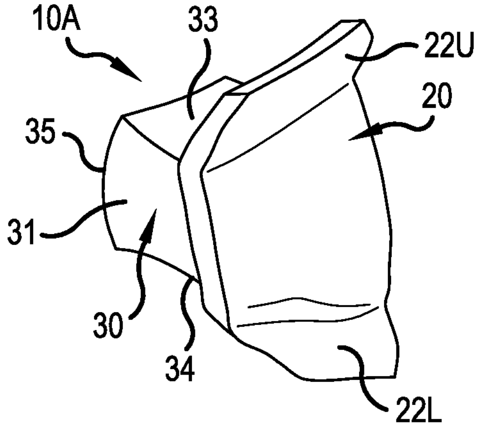
FIG. 5A graphically illustrates a perspective view the plated implant from the proximal side of the plate component thereof.
Figure 5B:
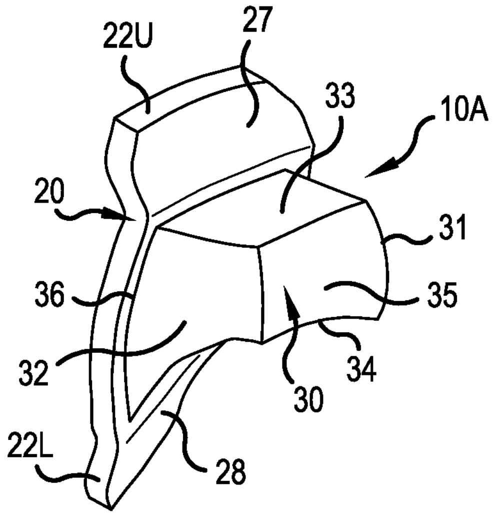
FIG. 5B graphically illustrates another perspective view of the plated implant of FIG. 5A from the distal side thereof, similar to FIG. 4B.

FIGS. 4A and 4B graphically illustrate the first embodiment of the implant 10 that includes an insert component (30) without the plate component (20), and is referred to as the plug implant 10. FIGS. 5A and 5B graphically illustrate the second embodiment of the implant 10A that is referred to as the plate implant. The plated implant 10 has two components: an insert 30 configured or shaped to fit into the cavity formed by the defect or cavity created to provide a specific shape for treatment if the defect cavity indeed needs to be treated, such as surgically removing parts thereof or manually shaped to create a particular geometrical space, before anchoring the insert in the defect IVD; and an external plate (hereafter "plate") 20 to facilitate connection to the spine. Both the plate implant 10 and the plug implant 10A can share the same the insert component. That is, the insert 30 of these embodiments can have the same configuration and composition.

The implant 10, 10A can be designed within the manufacturability constraints. In this respect, the geometry can be configured to be compatible with common bio-fabrication techniques, such as additive manufacturing (e.g., fused deposition modelling, such as 3D printing, and melt-electrowriting, etc.) and casting in a mold. The implant 10, 10A can be also designed with consideration to surgical feasibility, namely minimizing the implant footprint to reduce surgical exposure, dissection requirements, and retraction of the spinal nerves to access the defect.

In designing the implant 10, geometries of the target animal spine can be used to create solid models of implant designs that conform to spine geometries. That is, the geometries of the implant can be matched to the original annular geometry. Here, an angle-ply laminate scaffold or lattice architecture of polycaprolactone fibers was developed to fabricate the implant with mechanical properties that can approximate the pertinent mechanical properties of native AF tissue.

Specifically, the implants 10, 10A each include the insert 30, which is configured to occupy or fit into the cavity in the defect. The plated implant 10 further includes the plate 20, which is designed to facilitate surgical attachment of the implant to the FSU that includes the adjacent vertebral bodies (e.g., L4 L5) of the FSU with screws for example.

Both components, namely the plate 20 and the insert 30, can be designed and engineered to include biodegradable content, cellular content, drugs, or other biological content, whether directly incorporated into the structure during manufacture or added after the implant structure is formed. The insert 30 is configured to occupy the fissure/tear area of the defect and facilitate regeneration of annular tissue around and in the insert, as well as to transfer loads.

The insert 30 itself can be attached to the inner surfaces of the spine, such as using orthopaedic hardware (e.g., screws), sutures, and bio-adhesives. Although different geometric shapes can be used, the illustrated insert 30, for example, is hexahedron in shape, with six sides providing six faces, such as cubic, rectangular cuboid, truncated (square or rectangular) pyramid, parallelepiped, and rhombohedron configuration. Each of the six sides can be flat (see FIGS. 6A-6C and 7A-7C) or contoured (see FIGS. 4A-4B and 5A-5B). Moreover, the fabricated shape can be deformed, such as using heat, to obtain the desired shape conforming to the fissure/tear in the defect IVD.

Referring to FIGS. 4A and 4B, the fabricated plug implant 10 can include a first face 31, a second face 32 spaced from the first face 31, a third face 33, a fourth face 34 spaced from the third face 33, a fifth face 35 and a sixth face 36 spaced from the fifth face 35, which all can interface with the defect area of the defect IVD. The third and fourth faces 33, 34 extend between the first and second faces 31, 32, and the fifth and sixth faces 35, 36 extend between the first, second, third, and fourth faces to form the hexahedron shape for example. The insert 30 is inserted into the AF from the side of the fifth face (distal end).

Referring to FIGS. 5A and 5B, the plate 20 of the plate implant 10A is disposed on the side of the sixth face 36, and is configured to be attached to the outer surface of the spine, such as the vertebral bodies, cartilage endplates, and/or adjacent disc tissue to maintain the insert 30 in position. The plate 20 facilitates surgical attachment of the implant.

In the plate implant 10A, the plate 20 can be integrated part of the sixth face 36 and can extend outwardly (e.g., axially and circumferentially relative to the FSU) beyond the perimeters of the sixth face 36 bordering with the first, second, third, and fourth faces 31, 32, 33, and 34. Upper and lower wings 22U, 22L extend outwardly (axially in relation to the FSU) from the side of the third and fourth faces 33, 34, respectively. Moreover, the wings 22U, 22L provide surfaces 27, 28 on the side facing the FSU to provide additional areas that can be fused or attached thereto using bio-adhesive. The wings 22U, 22L are configured to be attached to the FSU, such as the vertebral bodies of the FSU.

The implant 10, 10A can be, for example, fabricated via three-dimensional fiber deposition (3DF), such as 3D printing, with fibrous architecture, such as scaffold/lattice configuration, that can replicate the desirable mechanical properties of native AF. Specifically, the implant can be made of an angle-ply laminate providing a 3DF scaffold configuration (e.g., mesh or lattice) with lamellae in the axial-circumferential direction. Only as an example, the scaffold structure can be fabricated using the following parameters: fiber angle=±34° from the circumferential direction in relation to the IVD, fiber spacing=1.0 mm, layer height=175 μm, and approximately 100-500 μm in nominal diameter. The number of layers is dependent on the fiber size and size of the defect that is being replaced/filled. The implant architecture can be, for example, generated using a combination of BioCAD software (RegenHU, Villaz-Saint-Pierre, Switzerland) and a custom g-code algorithm (Python 2.7, Python Software Foundation, USA) for 3D printing.

In one embodiment, the implant 10, 10A can be fabricated, via 3DF, from polycaprolactone (PCL) (average Mn 80,000, Sigma Aldrich, St. Louis, MO, USA), for example, using a 3DBiodiscovery bioprinter (HM-100 module, RegenHU Ltd., Villaz-Saint-Pierre, Switzerland; 27 gauge nozzle), for example. To achieve high quality fiber deposition throughout the print, the substrate temperature should be controlled, as is typical with 3D printing. The specific fiber diameters of the 3DF process can be measured from test samples from 2 layers of fibers, as illustrated in FIG. 8A for example, using a transmitted light microscope (Olympus BH-2, Tokyo, Japan) and Image Pro software (Media Cybernetics, Silver Spring, Maryland, United States).

Figure 8A:
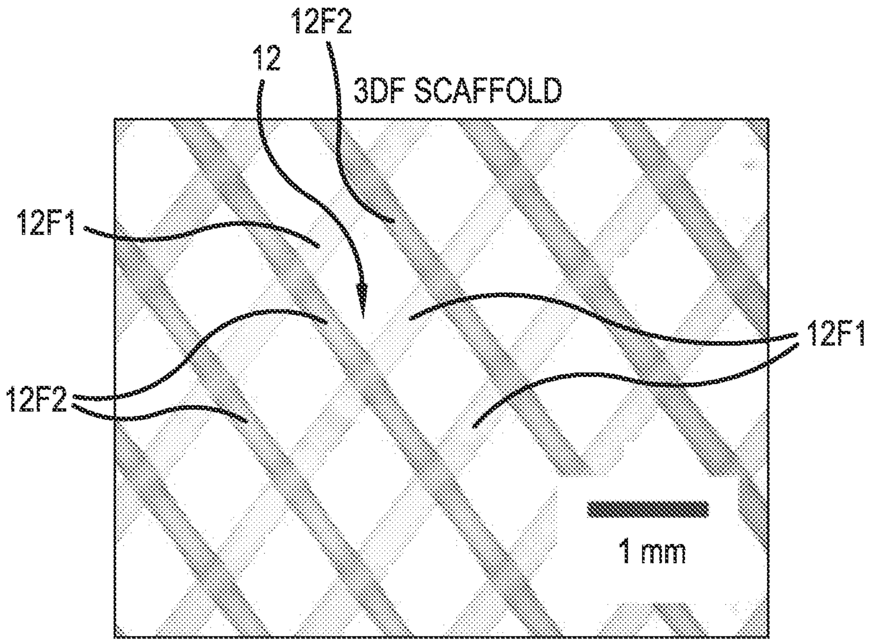
FIG. 8A shows an example microscope image of fibers configured via three-dimensional fiber deposition (3DF) and the relative scale (1 mm) of the 3DF fibers.

FIG. 8A is shows an example microscope image of fibers configured via three-dimensional fiber deposition (3DF) and the relative scale (1 mm) of the 3DF fibers, showing a first fibrous scaffold structure 12 formed of two layers of first fibers. In the one embodiment, as illustrated in FIG. 8A, the first fibrous scaffold structure 12 can include a first layer of first fibers 12F1 arranged parallelly spaced apart at a first spacing (e.g., 1 mm), and a second layer of additional first fibers 12F2 (same fibers as 12F1) arranged spaced apart at the first spacing and arranged an angle, which can be perpendicular, or at any orientation, relative to the first fibers 12F1 of the first layer.

Figure 8B:
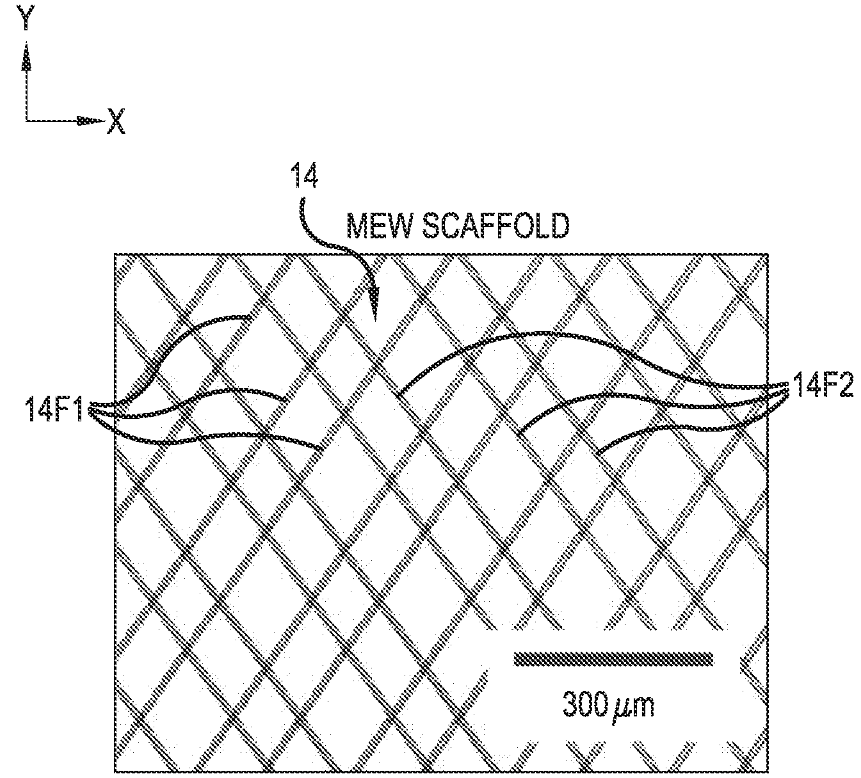
FIG. 8B shows an example microscope image of fibers configured via melt electrowriting (MEVV) and the relative scale (300 um) of the MEW fibers.

FIG. 8B shows an example microscope image of fibers configured via melt electrowriting (MEVV) and the relative scale (300 um) of the MEW fibers, showing a second fibrous scaffold structure 14 formed of two layers of second fibers. The second fibrous scaffold structure 14 can include a third layer of second fibers 14F1 arranged spaced apart at a second spacing, and a fourth layer of additional second fibers 14F2 (same fibers as 14F1) arranged spaced apart at the second spacing and arranged an angle, which also can be perpendicular, or at any orientation, relative to the second fibers 14F2 of the third layer.

Figure 8C:
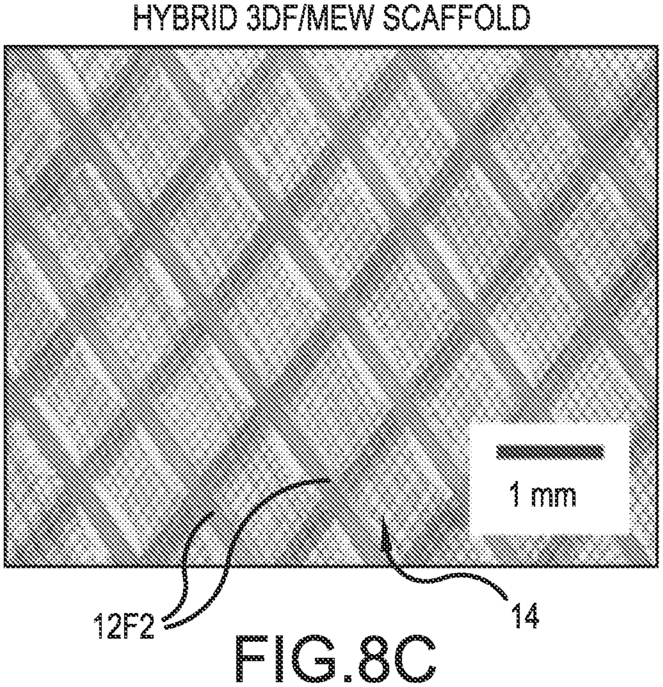
FIG. 8C shows an example microscope image of fibers configured via hybrid 3DF/MEW architecture and the relative scales (1 mm) of the 3DF/MEW fibers.
Figure 8D:
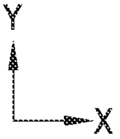
FIG. 8D shows an example microscope image of the hybrid 3DF/MEW configuration of FIG. 8C in the same relative scale (1 mm) but enlarged.
Figure 8D:
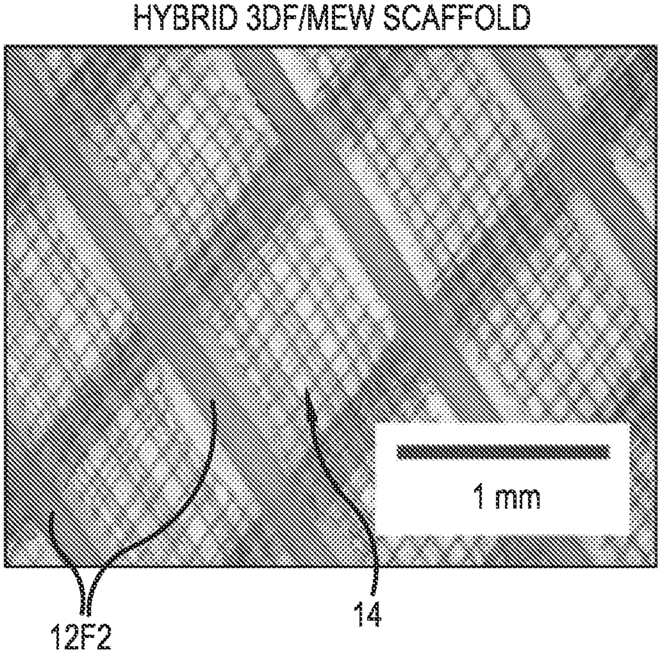

FIG. 8C shows an example microscope image of fibers configured via hybrid 3DF/MEW architecture and the relative scales (1 mm) of the 3DF/MEW fibers, namely showing another embodiment of the hybrid architecture that can be used to fabricate the implant 10, 10A. FIG. 8D shows an example microscope image of the hybrid 3DF/MEW configuration of FIG. 8C in the same relative scale (1 mm) but enlarged. In FIGS. 8A-8D, the x- and y-directions respectively represent the axial and circumferential directions in relation to the defect IVD.

Referring to FIGS. 8C-8D, in a hybrid embodiment, the implant 10, 10A can be fabricated using the multiscale hybrid fiber architecture, combining the same 3DF architecture structure of FIG. 8A with sheets of melt electrowritten (MEVV) fibers (see FIG. 8B), which are thinner than the fibers formed by 3DF, to yield a hybrid implant with a hybrid scaffold/lattice architecture. The MEW fiber material also can be PCL. But the fiber material for 3DF and MEW need not be the same for the hybrid implant. The sheets of MEW fibers can be fabricated in an angle-ply laminate architecture. Again, only as an example, the scaffold structure can be fabricated using the following parameters: fiber angle=±34° from the y-direction, fiber spacing=0.1 mm, number of bilayers=20, and approximately 5-100 μm in nominal diameter. Again, the number of layers can vary depending on the fiber size and size of the defect that is being replaced/filled. For example, a MEW toolhead (MESW module and 3DBiodiscovery printer, RegenHU Ltd., Villaz-Saint-Pierre, Switzerland) can be used to fabricate sheets of MEW.

In fabricating the hybrid implant, MEW sheets of at least two-layered MEW scaffold structure can be produced in advance, before the 3DF fabrication. During the fabrication of the 3DF scaffold structure 12, a first layer of a desired pattern can be formed by depositing a molten stream of polymer on a substrate (from which the formed implant is removed after its formation). A second layer of the 3DF structure 12 can be formed by depositing a molten stream of polymer with a desired pattern on the (now cooled and solid) bottom layer of polymer. When the hot polymer (e.g., PCL) meets the solid cold layer, localized melting occurs, essentially bonding the two layers together at these crossing points. This process can be repeated to form a desired number of layers fused by localized melting of one layer to the next when the top layer is laid on top of the bottom layer. The MEW sheets can be fabricated similarly but using melt electrowriting (thinner fibers).

During the 3DF fabrication, one of the prefabricated MEW sheets can then be disposed between 3DF scaffold (e.g., between adjacent fibers 12F2 as arranged as illustrated in FIGS. 8C and 8D, or other patterns, such as every other adjacent fibers). The MEW sheets can be applied between each layer or every other layer of the thus formed 3DF structure, or in any pattern that would promote tissue growth. After the 3DF fabrication of the implant is completed, the implant can be heated to fuse the fibers of the two fiber scaffold structures 12, 14.

In FIG. 8C-8D, one MEW sheet of the second fibrous scaffold structure 14 is disposed over the first layer, between adjacent first fibers 12F2 of the second layer, so that the one sheet extends along a length of the adjacent first fibers 12F2 of the second layer. The same steps can be repeated to disposes other MEW sheets. The fibers of the 3DF scaffold structure 12 have a larger nominal diameter than the fibers of the MEW sheets, and the first spacing is larger than the second spacing. After the desired number of layers of 3DF scaffold structure and the MEW sheets have been applied, the thus fabricated implant is heated to fuse the fibers of the 3DF scaffold structure 12 to the fibers of the MEW scaffold structure 14.

Additive manufacturing via 3DF can yield scaffold structures with consistent mechanical properties, and it may be possible to tailor these mechanical properties to replicate the continuum-level mechanics of native AF. But it remains unclear whether physiological loading of these scaffolds will be sufficient to stimulate progenitor cells to a fibrocartilaginous phenotype. The large scale of 3DF fibers may limit their ability to interact with resident cells in a TE scaffold and influence tissue regeneration. On the other hand, the smaller fibers generated from MEW can provide a greater functional relevance to the resident cells as MEW scaffold fibers have a similarity in scale to natural collagen fibers and yield a substantially larger surface area per unit volume in comparison to 3DF scaffold structures. Accordingly, combining 3DF fibers and MEW fibers in a tissue engineering strategy can beneficially leverage the mechanical and biological advantages of both fiber scales.

If the nominal diameter of the fabricated fibers is smaller than the desired fiber diameter, the biaxial mechanics of the fabricated implant may not match the designed mechanical properties. Indeed, computational work on the biaxial mechanics of angle-ply laminate scaffolds shows that a smaller fiber diameter can reduce the overall scaffold compliance and increase the asymmetry of the biaxial stiffnesses (i.e. axial-to-circumferential biaxial stiffness ratio). Moreover, computational modelling can be used to predict the desired implant parameters for delivering the desired mechano-regulatory stimulus to resident cells to promote growth.

Figure 6A:
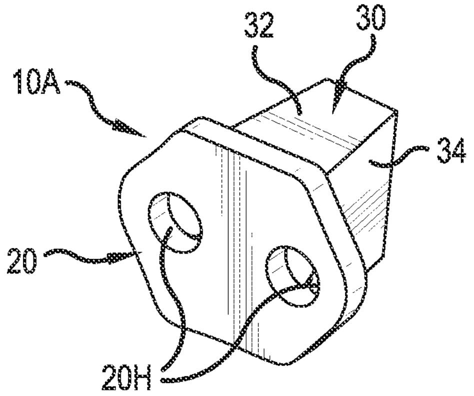
FIGS. 6A-6C graphically illustrate a digital geometry of the plated implant generated from a graphic software.
Figure 6B:
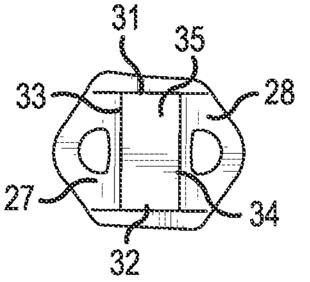
Figure 6C:
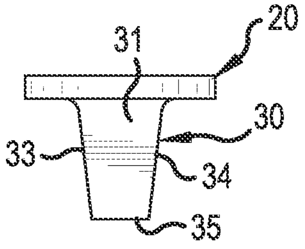
Figure 7A:
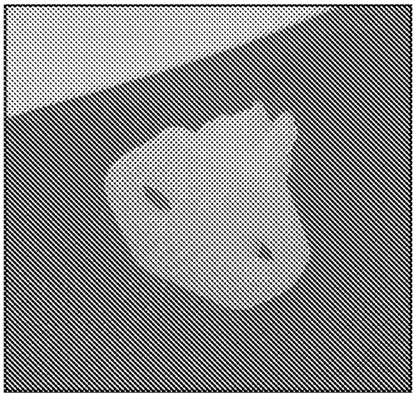
FIGS. 7A-7C are images of the fabricated plated implant according to an angle-ply fiber architecture (scaffold configuration) using the digitally generated configuration of FIGS. 6A-6C.
Figure 7B:
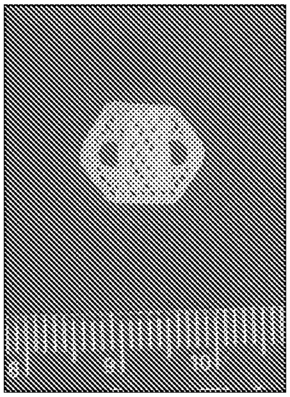
Figure 7C:
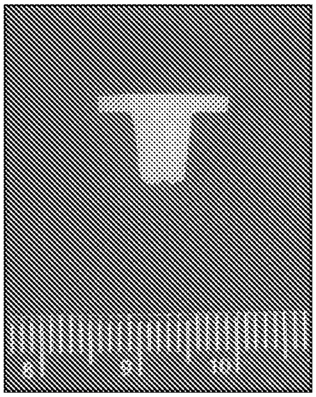

FIG. 6A graphically illustrates a perspective view of the plate implant 10A, FIG. 6B graphically illustrates a front view from the distal side of the plate implant 10A, and FIG. 6C graphically illustrates an elevational view of the plate implant 10A. FIG. 7A shows an image of the fabricated plate implant 10A corresponding to FIG. 6A, FIG. 7B shows an image of the fabricated plate 10A corresponding to FIG. 6B, and FIG. 7C shows an image of the fabricated plate 10A corresponding to FIG. 6C. Basically, FIGS. 6A-6C and FIGS. 7A-7C show the relationship between the digital geometry and the fabricated plated implant 10A formed using digital geometry in an angle-ply fiber scaffold architecture using the 3DF (FIG. 8A). The fabricated implant 10A can include holes 20H for insertion of fasteners, such as screws, and can be deformed into a shape desired. The desired scaffold architecture can be generated using a custom algorithm and printed.

The present embodiments of the implant 10, 10A each can include a biodegradable, additive manufactured implant with a fibrous scaffold architecture to mimic the native collagen organization in the AF. The biomechanical efficacy of such implants can be evaluated, for example, in a cadaveric ovine lumbar spine model. The ovine model for lumbar spine treatments is a widely-accepted, well-established translational model that closely reflects the physiological scale and mechanical loading of the human spine.

Multi-scale fibrous scaffolds can be leveraged to augment the manufacturability and mechanical performance of large fibers and the biological relevance of smaller scale fibers, as used in the hybrid implant. Combined with biodegradable materials, such as polycaprolactone (PCL), the hybrid scaffold architecture can be designed and fine-tuned to control the acute-phase spinal biomechanics while stimulating regeneration to prevent reherniation in the long-term.

The implant 10, 10A can be stabilized in situ, such as via screws, sutures, bio-adhesives, etc. When designing implant attachment strategy, it is important to consider the adjacent disc tissue, as well as promoting enhanced tissue regeneration to reproduce the pertinent mechanical properties of healthy AF tissue. But the implant attachment areas can be more critical modulator of implant loading in comparison to implant design. Tailoring of the cohesive attachment stiffness and increase of the implant compliance was found to facilitate control of the implant load state to a meet a proposed target for enhanced tissue regeneration.

Although large animal models provide a suitable translational platform to assess IVD repair strategies, and the ovine model is well-established translational model for the human spine, it is prohibitively time and resource intensive to study numerous design iterations with sufficient group sizes for statistical power. Further, it is experimentally challenging to characterize the mechanical loading of an implant, which loading dictates the complex, three-dimensional cellular micromechanical environment (CME) within the implant, which is a critical regulator of tissue regeneration.

To address the limitations of experimental animal models, computational methods, such as finite element analyses, can be utilized to efficiently predict how changes in implant design and surgical approach may alter the biomechanics and resultant implant micromechanics. For example, a computational model can predict the influence of a complete change of implant geometry or a small perturbation to the implant attachment technique. These perturbations may represent intentional changes to the surgical approach, variability among the population, or reasonably expected variability during surgical implementation.

Predictions from computational methods facilitate high-throughput evaluation of design modifications to identify critical design features and drive an efficient and effective experimental approach to AF repair. The commercial FE package ABAQUS (Dassault Systèmes SIMULIA, Johnston, RI) can be used to conduct the study using an FE model of a human FSU (lumbar function spine unit) isolated from an existing FE model of the lumbar spine. The geometries of the implant can be created in Solidworks (2016 SP4.0, Dassault Systèmes, Vélizy-Villacoublay, France) to exactly conform to the partial discectomy and spinal geometry.

The implant geometry can be meshed with a constant element size (i.e., nodal seed size remains constant throughout the geometry). A mesh convergence analysis can be conducted by loading the spine in flexion with the implant assumed to be perfectly bonded to all mating surfaces of the spine. An appropriate seed size can be selected based on convergence of the strain energy in the implant and computational time. The selected mesh size can be also used for analysis with the insert geometry.

Referring to FIGS. 4A-6C, which graphically illustrate the plug and plated implants showing the surfaces and faces that can be directly adhered to the IVD area being treated, there are different ways to attach the implant to the FSU, including (1) the external attachment using the plate 20 of the plate implant 10A, which includes (a) a screw mode where the plate component is attached to the vertebral bodies (e.g., L4, L5) just using screws, and (b) a plate mode where all contact surfaces 27, 28 of the plate 20 are adhered to the mating spine surfaces without using screws; (2) the internal attachment using the plug implant 10, which includes four different modes of attaching the insert component the implant, including (c) a no-bonding mode of any faces/surfaces (free float), (d) a circumferential bonding mode where only the opposing circumferential (in relation to the FSU) faces 31, 32 are bonded to the adjacent AF tissue of the IVD, (e) an axial bonding mode where only the opposing axial faces (in relation to the FSU) 33, 34 are bonded to the adjacent cartilaginous endplate (CE) tissues of the IVD, (f) a combined mode, where both the axial and circumferential faces 31, 32, 33, and 34 are bonded to the respective AF and CE tissues of the IVD; (3) the combination attachment, including a full mode wherein the surfaces/faces 31, 32, 33, 34, and 35 of the insert 30 and 27 and 28 of the plate 20; and (4) attachments (1)-(3) using bio-adhesive.

Available bio-adhesives can be evaluated for suitability. If no bio-adhesive is used, then the internal surfaces of the implant is not directly bonded to the native tissues; the implant is only kept in place initially by attaching the plate to any of the vertebrae, the IVD, including the CE and IVD tissue, via screws or other hardware, or other suitable attachment methods. Moreover, the implant and/or insert itself also can be internally secured to the IVD using other suitable attachment methods, other than bio-adhesive.

It has been found that the axial loading is strongly dependent on whether or not the internal axial face was attached to the vertebral endplate. In this respect, the internal implant attachment may be highly desirable for load transferring, which the external attachment cannot reproduce. Attachment of the internal circumferential face can increase the circumferential strains in the region of interest (ROI). Moreover, the circumferential attachment of the implant to the adjacent AF tissue can control the biaxial tension state and, subsequently, the regenerative environment of the implant. Moreover, continuity of the fibrous component of the AF can play a mechanical role in the IVD. Accordingly, the implant attachment in the circumferential direction can be more desirable to restore the mechanical continuity (i.e., more homogeneous load transfer) between the implant and the fibrous component of the adjacent AF tissue.

The attachment conditions, with all faces prescribed as either perfectly bonded (i.e., 100% bonding between the implant and the tissue to which it is attached) or non-bonded, are useful to understand the range of influence of implant attachment on the ROI load state. But perfectly bonded attachment conditions may not be feasible in practice, as all tensile interfaces between the implant and the spine must have some attributed bonding stiffness. Screws or sutures can fix the plate 20 to the spine with a relatively high stiffness, which may be effectively similar to a perfect bond. But at interfaces where screws or sutures are not feasible (e.g., due to obstruction of the regenerative site or lack of surgical access) the implant can be bonded to the spine via a bio-adhesive. At high cohesion stiffnesses (109 to 1010 Pa), relatively large implant loads can be generated in comparison to the idealized attachment condition. But it has been reported that most bio-adhesives that have been developed currently only have stiffness in the range of 104 to 107 Pa. In this range of cohesive stiffness, only minor loads can be generated in the implant. Accordingly, it would be desirable to provide bio-adhesives with high-stiffness and high-strength.

For regenerating the AF, it is desirable to control the load state within the implant to generate a cellular micromechanical environment that is conducive for repair. Two possible rationales for these load targets are: (1) reproduce the loading of the intact AF that regulates homeostasis of healthy AF tissue and (2) generate implant loading that generates an optimal cellular micromechanical environment for AF regeneration. Regardless of which rationale is used, is it advantageous to have a surgical strategy that can control and produce the target loading state.

The configuration and stiffness of the implant attachment can have the greatest influence on the implant loading. Additionally, an increase in the implant compliance can increase the magnitude of implant loading. By combining these parameters, the ROI load state can be tailored to meet the desired target. Overall, these data indicate that bio-adhesives can improve the implant loading and, ultimately, the regenerative potential of the repair strategy.

Given the present disclosure, one versed in the art would appreciate that there may be other embodiments and modifications within the scope and spirit of the present invention. Accordingly, all modifications attainable by one versed in the art from the present disclosure within the scope and spirit of the present invention are to be included as further embodiments of the present invention. The scope of the present invention accordingly is to be defined as set forth in the appended claims.

What is claimed is:

1. A biocompatible implant for repairing a defect in annulus fibrosus (AF) of an intervertebral disc (IVD) disposed in a functional spinal unit (FSU), the implant comprising:

an insert providing at least a first face and a second face, which is spaced from the first face, configured to interface with tissues in a gap occurring at the defect of the AF, wherein the insert comprises a plurality of layers of fibrous material providing a first fibrous scaffold structure and a second fibrous scaffold structure that is different from the first fibrous scaffold structure, wherein the first fibrous scaffold structure includes:

a first layer of first fibers arranged spaced apart at a first spacing; and a second layer of additional first fibers arranged spaced apart at the first spacing and arranged at an angle to the first fibers of the first layer, wherein the second fibrous scaffold structure includes:

a third layer of second fibers arranged spaced apart at a second spacing; and a fourth layer of additional second fibers arranged spaced apart at the second spacing and arranged at an angle to the second fibers of the third layer, wherein the second fibrous scaffold structure is disposed over at least the first or second layer, between adjacent first fibers of the second or first layer, so that the second fibrous scaffold structure extends along a length of the adjacent first fibers of the second or first layer, wherein the first fibers have a larger nominal diameter than the second fibers, and wherein the first spacing is larger than the second spacing.

2. The biocompatible implant according to claim 1, wherein:

the first spacing is 1.0 mm and a nominal diameter of the first fibers is in a range of 100-500 μm, and the second spacing is 0.1 mm and a nominal diameter of the second fibers is in a range of 5-100 μm.

3. The biocompatible implant according to claim 1, wherein:

the second fibrous scaffold structure forms at least one sheet, a plurality of sheets of the second fibrous scaffold structure are fused to the first fibrous scaffold structure.

4. The biocompatible implant according to claim 1, wherein the first face and the second face are spaced apart in a circumferential direction of the IVD, in a state where the insert is disposed in the AF.

5. The biocompatible implant according claim 4, further comprising:

a plate connected to the insert, wherein the plate also includes the first fibrous scaffold structure and the second fibrous scaffold structure, and wherein the plate includes upper and lower wings configured to secure to the FSU that includes the IVD to be repaired.

6. The biocompatible implant according to claim 1, wherein the first face and the second face are spaced apart in an axial direction of the IVD, in a state where the insert is disposed in the AF.

7. The biocompatible implant according claim 6, further comprising:

a plate connected to the insert, wherein the plate also includes the first fibrous scaffold structure and the second fibrous scaffold structure, and wherein the plate includes upper and lower wings configured to secure to the FSU that includes the IVD to be repaired.

8. The biocompatible implant according to claim 1, wherein:

the insert includes a third face, a fourth face spaced from the third face, a fifth face, and a sixth face spaced from the fifth face, the third and fourth faces are disposed between the first and second faces, the fifth face and the sixth face extend between the first, second, third, and fourth faces and form a hexahedron shape with six sides.

9. The biocompatible implant according to claim 8, further comprising:

a plate disposed on a side of the sixth face, wherein the plate also includes the first fibrous scaffold structure and the second fibrous scaffold structure, and wherein the plate includes upper and lower wings, extending axially outwardly respectively from a side of the third face and a side of the fourth face, and configured to secure to the FSU that includes the IVD to be repaired.

10. The biocompatible implant according to claim 1, wherein at least one the first or second fibers comprise polycaprolactone.

11. A method of manufacturing the biocompatible implant according to claim 1, the method comprising:

forming the first fibrous scaffold structure including the first layer and the second layer by:

forming the first layer by arranging the first fibers spaced apart at the first spacing;

forming the second layer over the first layer by arranging the additional first fibers spaced apart at the first spacing at an angle to the first fibers of the first layer;

forming each of a plurality of sheets of the second fibrous scaffold structure including the third layer and the fourth layer by:

forming the third layer by arranging the second fibers that have a smaller nominal diameter than the first fibers spaced apart at the second spacing that is smaller than the first spacing; and forming the fourth layer over the third layer by arranging the additional second fibers spaced apart at the second spacing at an angle to the second fibers of the third layer; and disposing one sheet, among the plurality of sheets of the second fibrous scaffold structure, over at least one of the first or second layer, between adjacent first fibers of the second or first layer, so that the one sheet extends along a length of the adjacent first fibers of the second or first layer.

12. The method according to claim 11, wherein:

the first and second layers are formed by three-dimensional fiber deposition, and the third and fourth layers are formed by melt electrowriting.

13. The method according to claim 12, further comprising heating the implant to fuse the sheets of the second fibrous scaffold structure to the first fibrous scaffold structure.

14. A method of repairing a defect in annulus fibrosus (AF) of an intervertebral disc (IVD) disposed in a functional spinal unit (FSU) using the biocompatible implant according to claim 1, the method comprising:

disposing the insert inside the gap at the defect of the AF so that the first face and the second face interface with adjacent tissues at the gap and the first face and the second face are spaced along a circumferential direction of the IVD; and securing the insert to the FSU.

15. The method according to claim 14, wherein:

the insert includes a third face, a fourth face spaced from the third face, a fifth face, and a sixth face spaced from the fifth face, the third and fourth faces are disposed between the first and second faces, the fifth face and the sixth face extend between the first, second, third, and fourth faces and form a hexahedron shape with six sides.

16. The method according to claim 15, further comprising:

securing at least one of:

the first face and the second face to the IVD; or the third face and the fourth face to the IVD, wherein each of the third face and the fourth face is configured to interface with one of cartilaginous endplates of the IVD at top and bottom sides thereof.

17. The method according claim 15, wherein:

the biocompatible implant further includes a plate extending from the sixth face, wherein the plate also includes the first fibrous scaffold structure and the second fibrous scaffold structure, and wherein the plate includes upper and lower wings configured to secure the biocompatible implant to the FSU that includes the IVD to be repaired.

18. The method according to claim 17, further comprising:

securing the upper and lower wings to the FSU using at least one of screws or bio-adhesive.

19. The method according to claim 17, further comprising:

securing using bio-adhesive:

the first face and the second face to the IVD;

the third face and the fourth face to the IVD;

the upper and lower wings to the FSU.

* * * * *